(12) United States Patent
Librizzi et al.

(10) Patent No.: US 6,830,755 B2
(45) Date of Patent: Dec. 14, 2004

(54) METHOD FOR RELAXING HUMAN BEINGS USING PERSONAL CARE COMPOSITIONS

(75) Inventors: Joseph Librizzi, Neshanic, NJ (US); Benjamin Carl Wiegand, Newtown, PA (US); Teresita Diaz, Perth Amboy, NJ (US); Laura McCulloch, Kings Somborne (GB); John Hopkins, Newbury (GB); Theodore L. Barba, Old Brookville, NY (US); Anthony Joseph Leardi, Middletown, NY (US); Gerard William Appert, Kinnelon, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 10/218,774

(22) Filed: Aug. 14, 2002

(65) Prior Publication Data

US 2003/0064120 A1 Apr. 3, 2003

Related U.S. Application Data

(63) Continuation of application No. 09/676,876, filed on Sep. 29, 2000.
(60) Provisional application No. 60/157,371, filed on Oct. 1, 1999.

(51) Int. Cl.[7] .................................. A61K 9/00
(52) U.S. Cl. .................. 424/401; 424/70.1; 424/69; 424/443; 424/725; 424/736; 424/764; 424/765
(58) Field of Search ................ 424/401, 7.01, 424/69, 443, 725, 736, 764, 765

(56) References Cited

U.S. PATENT DOCUMENTS

| | | |
|---|---|---|
| 4,013,417 A | 3/1977 | Raffaele |
| 4,375,421 A | 3/1983 | Rubin et al. |
| 4,556,557 A | 12/1985 | Reichert |
| 4,597,885 A * | 7/1986 | Berry et al. ................ 510/135 |
| 4,657,690 A | 4/1987 | Grollier et al. |
| 4,664,835 A | 5/1987 | Grollier et al. |
| 4,668,513 A | 5/1987 | Reichert |
| 4,670,264 A | 6/1987 | Warren et al. |
| 4,671,959 A | 6/1987 | Warren et al. |
| 4,877,322 A | 10/1989 | Hill |
| 5,009,813 A | 4/1991 | Watanabe et al. |
| 5,063,062 A | 11/1991 | Greenspan et al. |
| 5,079,227 A | 1/1992 | Handjani et al. |
| 5,124,078 A | 6/1992 | Baust |
| 5,275,761 A | 1/1994 | Bergmann |
| 5,284,603 A | 2/1994 | Repinec, Jr. et al. |
| 5,304,112 A | 4/1994 | Mrklas et al. |
| 5,350,774 A | 9/1994 | Palou |
| 5,403,263 A | 4/1995 | Rodgers |
| 5,403,587 A | 4/1995 | McCue et al. |
| 5,466,446 A | 11/1995 | Stiefel et al. |
| 5,497,771 A | 3/1996 | Rosenheimer |
| 5,540,853 A | 7/1996 | Trinh et al. |
| 5,578,312 A | 11/1996 | Parrinello |
| 5,597,406 A | 1/1997 | Fiscer et al. |
| 5,597,407 A | 1/1997 | Fischer et al. |
| 5,607,980 A | 3/1997 | McAtee et al. |
| 5,614,553 A | 3/1997 | Ashmead et al. |
| 5,711,899 A | 1/1998 | Kawa et al. |
| 5,716,919 A | 2/1998 | Sano |
| 5,753,637 A | 5/1998 | Fried |
| 5,771,261 A | 6/1998 | Anbar |
| 5,789,953 A | 8/1998 | Au et al. |
| 5,792,739 A | 8/1998 | He et al. |
| 5,804,538 A | 9/1998 | Wei et al. |
| 5,849,310 A | 12/1998 | Trinh et al. |
| 5,855,884 A | 1/1999 | Theoharides |
| 5,871,757 A | 2/1999 | Cloughley et al. |
| 5,891,427 A * | 4/1999 | Mettler ................... 424/76.21 |
| 5,904,916 A | 5/1999 | Hirsch |
| 5,910,477 A | 6/1999 | Gordon |
| 5,916,576 A | 6/1999 | Dornoff et al. |
| 5,922,331 A | 7/1999 | Mausner |
| 5,958,462 A | 9/1999 | McLean |
| 5,965,502 A | 10/1999 | Balzer |
| 5,980,925 A | 11/1999 | Jampani et al. |
| 6,134,460 A | 10/2000 | Chance |
| 6,244,265 B1 | 6/2001 | Cronk et al. |
| 6,245,769 B1 | 6/2001 | Arvanitis et al. |
| 6,524,626 B2 | 2/2003 | Chen |
| 6,635,263 B2 | 10/2003 | Tanida et al. |
| 2002/0111529 A1 | 8/2002 | Allen Licht |

FOREIGN PATENT DOCUMENTS

| | | |
|---|---|---|
| AU | 579191 | 4/1986 |
| AU | 654850 | 5/1992 |
| AU | 664987 | 10/1992 |
| AU | 701232 | 12/1995 |
| AU | 723030 | 5/1996 |
| AU | 43839 | 5/1998 |
| AU | 730992 | 5/1998 |
| AU | 60334/98 | 8/1998 |
| CA | 2 153 313 | 8/1994 |
| CA | 2 155 766 | 8/1994 |
| CA | 2 127 348 | 1/1995 |
| CA | 2 127 657 | 1/1995 |
| CA | 2 167 174 | 1/1995 |
| CA | 2 216 964 | 10/1996 |

(List continued on next page.)

OTHER PUBLICATIONS

Johnson & Johnson Consumer Companies, Inc., U.S. patent application Ser. No. 10/012,627.

(List continued on next page.)

Primary Examiner—Thurman K. Page
Assistant Examiner—Konata M. George
(74) Attorney, Agent, or Firm—Erin M. Harriman

(57) ABSTRACT

This invention relates to a method of relaxing mammals comprising administering to said mammals a personal care composition which comprises an effective amount of a sensory fragrance that is effective in reducing cortisol levels and/or increasing sIgA levels.

10 Claims, No Drawings

FOREIGN PATENT DOCUMENTS

| | | |
|---|---|---|
| CA | 2247825 | 2/1997 |
| CA | 2244887 | 8/1997 |
| DE | 3445547 A1 | 7/1985 |
| EP | 0 347 306 | 12/1989 |
| EP | 681832 | 11/1995 |
| EP | 0 681 832 A2 | 11/1995 |
| EP | 0 713 860 B1 | 5/1996 |
| EP | 0 841 061 A2 | 5/1998 |
| EP | 978273 | 2/2000 |
| EP | 0 983 990 A2 | 3/2000 |
| EP | 1 082 960 A2 | 3/2001 |
| EP | 1198995 A1 | 4/2002 |
| FR | 2191878 | 2/1974 |
| FR | 2191878 | 3/1974 |
| FR | 2730634 A1 | 8/1996 |
| JP | 3284619 | 11/1991 |
| JP | 2973368 | 12/1991 |
| JP | 4077416 | 3/1992 |
| JP | 2548074 | 6/1994 |
| JP | 1972802 | 12/1994 |
| JP | 6-104621 | 12/1994 |
| JP | 9227399 A | 2/1996 |
| JP | 9-227399 | 9/1997 |
| JP | 9227400 A | 9/1997 |
| JP | 11-19076 | 1/1999 |
| JP | 11 19076 | 1/1999 |
| JP | 11 019076 A | 1/1999 |
| JP | 11 023579 A | 1/1999 |
| JP | 11-34688 A | 2/1999 |
| JP | 2000 275248 A | 10/2000 |
| WO | WO 94/07461 | 4/1994 |
| WO | WO 96/12468 A1 | 5/1996 |
| WO | WO 96/12468 | 5/1996 |
| WO | WO 96/25389 | 8/1996 |
| WO | WO 97/03646 | 2/1997 |
| WO | WO 97/28785 A1 | 8/1997 |
| WO | WO 97/30688 | 8/1997 |
| WO | WO 97/32560 A1 | 9/1997 |
| WO | WO 98/08846 A1 | 3/1998 |
| WO | WO 98/13022 | 4/1998 |
| WO | WO 98/27938 | 7/1998 |
| WO | WO 98/38973 | 9/1998 |
| WO | WO 99/09947 | 3/1999 |
| WO | WO 99/31511 A1 | 6/1999 |
| WO | WO 99/44577 | 9/1999 |
| WO | WO 9963883 A | 12/1999 |
| WO | WO 00/01360 | 1/2000 |
| WO | WO 01/98442 A | 12/2001 |
| WO | WO 02/49600 A1 | 6/2002 |
| WO | WO 02/49629 A2 | 6/2002 |
| WO | WO 02/62198 A2 | 8/2002 |

OTHER PUBLICATIONS

Johnson & Johnson Consumer Companies, Inc., U.S. patent application Ser. No. 10/012,626.

Johnson & Johnson Consumer Companies, Inc., U.S. patent application Ser. No. 60/256,812.

International Search Report dated Aug. 23, 2002 for PCT/US01/50757 (=WO 02/49629=JBP–570).

International Search Report corresponding to Int'l Appln. PCT/US00/27035.

"Biology of Beauty" article (pre Oct. 1999).

"Aromachology, the Science Behind the Fragrance" article (pre Oct. 1999).

Tube for Origins Diaper Service™ Balm (available before Oct. 1999).

Tube for Origins Love Me Tender™ lotion (available before Oct. 1999).

Tube for Origins Bare Hugs™ cream (available before Oct. 1999).

Bottle for Origins Baby Shower™ wash (available before Oct. 1999).

Package for Origins Short Cake™ bar (available before Oct. 1999).

Package for Origins Smooth Baby™ oil (available before Oct. 1999).

William J. Cunliffe, Acne, 1989, 1–11, Martin Dunitz Ltd., UK.

S. Cohen, T.Kamarck, R. Mermelstein, A Global Measure of Perceived Stress, Journal of Health and Social Behavior 1983, 385–396, vol. 24 (Dec.).

P. Brantley, C. Waggoner, G. Jones, N. Rappaport, A Daily Stress Inventory: Development, Reliability, and Validity, Journal of Behavioral Medicine, 1987:61–75, vol. 10, No. 1.

T.R. Cooper, H.R. Trunkfield, A.J. Zanella, W.D. Booth, An enzyme–linked Immunosorbent Assay for Cortisol in the Saliva of Man and Domestic Farm Animals, Journal of Endocrinology (1989) R13–R16.

A. Beck, G. Brown, N. Epstein, R. Steer, An Inventory for Measuring Clinical Anxiety: Psychometric Properties, Journal of Consulting and Clinical Psychology, 1988, 893–897, vol. 56, No. 6.

A. Buske–Kirschbaum, S. Jobst, A. Wustmans, C. Kirschbaum, W. Rauh, D. Hellhammer, Attenuated Free Cortisol Response to Psychosocial Stress in Children with Atopic Dermatitis, Psychosomatic Medicine, 1997:419–426, vol. 59.

A. Slominski, J. Wortsman, T. Luger, R. Paus, S. Solomon, Corticotropin Releasing Hormone and Proopiomelanocortin Involvement in the Cutaneous Response to Stress, Physiological Reviews, Jul. 2000:979–1020. vol. 80, No. 3.

M. Morohashi, M. Toyada, Y. Luo, S. Higaki, Cutaneous Neurologic Factors are Involved in the Pathogenesis of Acne, The Journal of Investigative Dermatology:820.,2000, vol. 114 (Abstract).

E. Aardal, A. Charlotte Holm, Cortisol in Saliva–Reference Ranges and Relation to Cortisol in Serum, European Journal Clin Chem, Clin Biochem 1995: 927–932, 33(No 12).

D. Watson, L. Clark, A. Tellegen, Development and Validation of Brief Measures of Positive and Negative Affect: The PANAS Scales, Journal of Personality and Social Psychology, 1988:1063–1070, vol. 54, No. 6.

O. Wolkowitz, V. Reus, A. Keebler, N. Nelson, M. Friedland, L. Brizendine, E. Roberts, Double–Blind Treatment of Major Depression with Dehydroepiandorsterone, Am. J. Psychiatry, Apr. 1999: 646–649, 156:4.

F. Dhabhar, B. McEwen, Enhancing versus suppressive effects of stress hormones on skin immune function, Proc. Natl. Acad. Sci. USA. 6(Feb. 1999):1059–1064., vol. 96.

P. Schulz, W. Schlotz, Trierer Inventar zur Erfassung von chronischem Stress (TICS), , Diagnostica 45, Heft 1, Hogrefe Veriag Gottingen 1999: 8–19 (With English Abstract).

M. Horowtiz, N. Wilner, W. Alvarez, Impact of Event Scale: A Measure of Subjective Stress,, Psychosomatic Medicine, (May 1979):209–218, vol. 41, No. 3.

P. Hunt, E. Gurnell, F. Huppert, C. Richards, A. Prevost, J. Wass, J. Herbert, V. Chatterjee, Improvement in Mood and Fatigue after Dehydroepiandrosterone Replacement in Addison's Disease in a Randomized, Double Blind Trial, The Journal of Clinical Endocrinology & Metabolism, 2000:4650–4656, vol. 85, No. 12.

M. Chren, R. Lasek, S.Flocke, S. Zyzanski, improved Discriminative and Evaluative Capability of a Refined Version of Skindex, a Quality–of–Life Instrument for Patients with Skin Diseases, Arch Dermaology, Nov. 1997:1433–1440, vol. 133.

K. Kabat–Zinn, E. Wheeler, T. Light, A. Skillings, M. Scharf, T. Cropley, D. Hosmer, J Bernhard, Influence of a Mindfulness Meditation–Based Stress Reduction Intervention on Rates of Skin Clearing in Patients with Moderate to Severe Psoriasis Undergoing Phototherapy (UVB) and Photochemotherapy(PUVA), Psychosomatic Medicine (1998):625–632, vol. 60.

J. Kiecolt–Glaser, R. Glaser, E. Strain, J. Stout, K. Tarr, J. Holliday, C. Speicher, Modulation of Cellular Immunity in Medical Students, Journal of Behavioral Medicine, (1986):5–21., vol. 9, No. 1.

N. Bolger, E. Schilling, Personality and the Problems of Everyday Life: The Role of Neuroticism in Exposure and Reactivity to Daily Stressors, Journal of Personality, Sep. 1991: 355–386, 59:3.

M. Sulzberger, S. Zaidens,Psychogenic Factors in Dermatologic Disorders, 1948:669–685.

A. Garg, M. Chren, L. Sands, M. Matsui, K. Marenus, K. Feingold, P. Elias, Psychological Stress Perturbs Epidermal Permeability Barrier Homeostasis, Implications for the Pathogenesis of Stress–Associated Skin Disorders, Arch Dermatol, (Jan. 2001)53–59., vol. 137.

E. Panconsesi, G. Hautmann, Psychophysiology of Stress in Dermatology:The Psychobiologic Pattern of Psychosomatics, Dermatologic Clinics, (Jul. 1996):399–421., vol. 14, No. 3.

C. Kirschbaum, D. Hellhammer, Salivary Cortisol in Psychobiological Research:An Overview, Neuropsychobiology 1989:150–169, vol. 22.

M. Denda, T. Tsuchiya, P. Elias, K. Feingold, Stress alters cutaneous permeability barrier homeostatis, Am. J. Physiol. Regulatory Integrative Comp. Physiol., 2000:R367–R372., vo. 278.

R. A. Dressendorfer, C. Kirschbaum, W. Rohde, F. Stahl, C.J. Strasburger, Synthesis of a Cortisol–Biotin Conjugate and Evaluation as a Tracer in an Immunoassay for Salivary Cortisol Measurement, J. Steroid Biochem, Molec. Biol. 1992, 683–692, vol. 43, No. 7.

A. Delongis, S. Folkman, R. Lazarus, The Impact of Daily Stress on Health and Mood:Psychological and Social Resources as Mediators, Journal of Personality and Social Psychology, 1988:486–495, vol. 54, No. 3.

G. Chrousos, P. Gold, The Concepts of Stress and Stress System Disorders: Overview of Physical and Behavioral Homeostasis, Stress and Stress Disorders–Chrousos & Gold, JAMA, Mar. 4, 1992:1244–1252.vol. 267, No. 9.

R. Sapolsky, Why Zebras Don't Get Ulcers, W. H. Freeman and Company, New York, 1998:1–18.

Tausk et al., Stress and the Skin, Arch Dermatol. Jan. 2001:78–82, vol. 137.

Scholzen, T., Armstrong, C.A., Bunnett, N.W., Luger, T. A. , Olerud, J.E., Ansel, J.C., Neuropeptides in the skin: interactions between the neuroendocrine and the skin immune system, Experimental Dermatology, 1998:7:81–96, Denmark.

Www.shiseido.co. , publicly available prior to Dec. 7, 2001. Bottle for JOHNSON'S® Bedtime Bath™ (Oct. 1999).

Badia, P., et al., "Some Effects of Fragrances on Sleep" Compendium of Olfactory Research 1982–1994 ["Compendium"]31–36 (1994).

Dember, William, et al., "Olfactory Stimulation and Sustained Attention" Compendium 39–46 (1994).

Saintigny, Gaelle, et al., "The use of Essential Oils to Stimulate the release of relaxing substances by human Ketatinocyes" XXIst IFSCC Int'l. Congress 2000, Berlin–Proceedings.

Clemens Kirschbaum and Dirk H. Hellhammer "Salivary Cortisol", Encyclopedia of Stress, vol. 3, pp 379–384.

Barbara Carlton, "In Quest for Prettiest Baby, Parents Snap up Pricey Kid's Cosmetics" Jun. 9, 2000, NewsEdge Insight ["Carlton"].

"Fussy Time" Calming baby bath aromatherapy. Cited in Jun. 9, 2000 NewsEdge Article.

Karen Douthwaite "Bringing Up Baby", Oct. 1999.

Arthur A. Stone, Donald S. Cox, Heiddis Valdimarsdottir and Lina Jandorf, John M. Neale, "Evidence that Secretory IgA Antibody is Associated with Daily Mood" Journal of Personality and Social Psychology, 1987, vol. 52, No. 5, 9988–993.

Clemens Kirschbaum and Dirk Hellhammer "Salivary Cortisol in Psychoneuroendocrine Research: Recent Developments and Applications" Psychoneuroendocrinology, vol. 19, No. 4, pp. 313–333, 1994.

Carlton, Barbara (as cited in Wall Street Journal B1 (Jun. 9, 2000).

Abstract JP 1185267 Geran Kaihatsu Kenk (1989) "Nasal Inhalation Instrument".

Abstract AU 9728425, Dobrincic. A (1998) "Soothing Calm Non Sting Herb Heal Strip . . . ".

English–Language Abstract of FR 2191878 (1974).

European Search Report, EP 03 25 0490 dated Jun. 23, 2003.

Shoji et. al., U.S. patent application Ser. No. 2003/005049 A1.

Johnson & Johnson Consumer Companies, Inc., U.S. patent application Ser. No. 10/357648.

Johnson & Johnson Consumer Companies, Inc., U.S. patent application Ser. No. 10/353525.

Johnson & Johnson Consumer Companies, Inc., U.S. patent application Ser. No. 10/378,384.

C. Kirschbaum, D. Hellhammer, Salivary Cortisol in Psychoneuroendocrine Research: Recent Developments and Applicantions, Psychoneuroendocrinology, 1994, 313–333, vol. 19, No. 4.

Heim, Christine et. al. "The potential role of hypocortisolism is the pathophysiology of stress–related boldiy disorders". Psychoneurocrinology, vol. 25 No. 1, Jan. 2000 pp. 1–35 XP002239756.

Schmidt–Reinwald A. et. al. "The corisol response to awakening in relation to different challenge tests and a 12–hour cortisol rhythm" Life Sciences. vol. 64, No. 18, Mar. 26, 1999 p. 1653–1660 XP002239757.

JP 01 185267 A (Geran Kaihatsu Kenk), Jul. 24, 1989 abstract.

AU 9728425 to Dobrincic, "Soathing, calming, non–stinging Herbal Strip," Abstract (Jan. 15, 1998).

Friess, Elisabeth et. al. "The hypothalamic–pituitary–adrenocoritcal system and sleep in man", Advances in Neuroimmunology, vol. 5, pp. 111–125, 1995.

Leigh, Terry J. et. al, "Factor Analysis of the St. Mary's Hospital Sleep Questionnaire", SLEEP 11(5), pp. 448–453, 1988.

Kollias, N. et. al. "A single Parameter, Oxygenated Hemoglobin can be used to Quanitity Experimental irritant–induced inflammation", The Journal of Investigative Dermatology, vol. 104 No. 3, pp 421–424, Mar. 1995.

Shaw, Christine R., "The perimenopausal Hot Flash: Epidemiology, Physiology, and Treatment", The Nurse Practitioner, vol. 22, No. 3, pp. 55–66, Mar. 1997.

Anarte, M.T., et. al. "Hormonal and psychological treatment::therapeutic alternative for menopausal women?" MATURITAS, 29, pp. 203–213, 1998.

Aromatherapy Workbook, Marcel Lavabre, pp. 74,75,84, 104, 131–132,139, 152 (1990).

Weil, Andrew, "Breathing–The Master Key to Self Healing" 2 CD Set (1999)–CD's attached.

XP002208946 & WO 01 98442 A (Shiseido Co. Ltd), Dec. 27, 2001 abstract.

XP002208807 & JP 11 019076 (Pola Chem Ind. Inc.) Jan. 26, 1999 abstract.

XP002208808 & JP 11 023579 (Pola Chem Ind. Inc.), Jan. 29, 1999 abstract.

AU 9465919 Emili, R. et al. (1995) (Abstract).

EPO Search Report for EPO Appl. No. 04251206.1 dated May 14, 2004.

* cited by examiner

METHOD FOR RELAXING HUMAN BEINGS USING PERSONAL CARE COMPOSITIONS

CROSS-REFERENCE TO RELATED APPLICATION

This Application is a continuation of U.S. application Ser. No. 09/676,876 filed on Sep. 29, 2000, which claimed the benefit of U.S. application Ser. No. 60/157,371 filed on Oct. 1, 1999, which are both incorporated by reference in their entireties herein.

FIELD OF THE INVENTION

This invention relates to administering personal care compositions to humans where said compositions contain sensory fragrances.

BACKGROUND OF THE INVENTION

Many currently marketed fragrant cosmetic products claim to have a "calming", "stimulating" or "relaxing" benefit to the user. Typically, these products possess fragrances that are purported to deliver these benefits. To support these claims, several methods have been employed to measure the effects of fragrance on physiological parameters with varying degrees of success and unfortunately, much of the evidence for these purported benefits is the subject of folklore, rather than science.

Cortisol is an adrenocortical hormone which can be found in the blood and the saliva of human beings. Cortisol is produced in the adrenal cortex and is involved in a number of neurological events. Some have found that the level of this hormone rises when an individual is subjected to psychological and physiological stress. Kirschbaum, C. & Hellhammer, D. H., "Salivary Cortisol in Psychoendocrine Research: Recent Developments and Applications"; Psychoendocrinology, Vol.19 No. 4, 1994, pp. 313–333.

Others have found that when adults are subjected to psychological stress (practicing arithmetic under stressful conditions) that their level of stress can be monitored by their salivary cortisol. Tanizawa, "A Method for the Determination of the Anti-Stress Effects of Fragrances" JP Patent No.11-19076. The same researchers have shown that if the same individuals were exposed to certain fragrances before the stressful event, their level of salivary cortisol levels would not be as high as when they were psychologically challenged without the fragrance. Id. In this study, the subjects were of the age where they could perform arithmetic calculations. In addition this study showed that not all fragrances were effective at reducing the stress induced release of cortisol. Fragrances with lavender oil or mint oil successfully lowered cortisol levels, while the fragrance with skatole had the opposite effect.

Aside from cortisol levels, there are other indicators that correlate with stress levels in human beings, such as secretory immunoglobulin A (sIgA). See EP 978273 (an increase in sIgA signifies an increase in relaxation) and Stone, et al., "Evidence that Secretory IgA antibody is associated with daily mood," 52(5) J. Personality and Social Psychology 988–93 (1987)("Stone"). sIgA is a secretory immunoglobulin that is found in the saliva of human beings.

It would be desirable to find other fragrance compositions that are capable of reducing stress, and in particular to find such fragrance compositions that are capable of reducing stress in children. More specifically, when children, i.e., those having an age of about 1 day to about 12 years, are subjected to stressful situations, they do not smile, they cry and they do not sleep well. It would be most advantageous for the children if there were a method of reducing these physical symptoms of stress.

SUMMARY OF THE INVENTION

This invention relates to a method of relaxing a mammal comprising administering to said mammal a personal care composition which comprises an effective amount of a sensory fragrance, wherein the personal care composition is capable of reducing the cortisol level of the mammal by about 0.1% to about 75% and/or increasing the sIgA level of the mammal by about 10% to about 150%.

Another aspect of the present invention includes a method of relaxing a mammal comprising administering to said mammal a personal care composition which comprises an effective amount of a sensory fragrance, the sensory fragrance being comprised of, based upon the total weight of the sensory fragrance, from about 0.1% to about 8% of an essential oil portion and from about 92% to about 99.9% of an odoriferous portion, the odoriferous portion containing one or more benzenoid materials, alcohol materials, ester materials, aldehyde materials, ketone materials, or mixtures thereof, wherein the personal care composition is capable of reducing the cortisol level of the mammal by about 0.1 to about 75% and/or increasing the sIgA level of the mammal by about 10% to about 150%.

DETAILED DESCRIPTION OF THE INVENTION

This invention relates to a method of calming mammals including humans, and in particular those having an age of from about 1 day to about 12 years, comprising administering to the mammals a personal care composition which comprises an effective amount of a sensory fragrance. The preferred age of a human who is calmed by this invention is 1 week to 5 years, more preferably 1 week to 3 years, most preferably between about 1 week to about 2 years.

As used herein "calming" refers to the psychological aspects of well being, namely the feeling of good will, relaxation and/or the absence of malice and aggravation.

As used herein, "mammals" include any of a class of warm-blooded higher vertebrates that nourish their young with milk secreted by mammary glands and have skin usually more or less covered with hair, and non-exclusively includes humans, dogs and cats.

The term "administering" refers to the (i) inhalation of a topically applied personal care composition; (ii) inhalation of the vapors which are released when a personal care composition is dissolved or dispersed in a liquid vehicle such as water, or (iii) inhalation of vapors which are released when a personal care composition is dispersed, sprayed, melted or burned.

The term "effective amount" refers to the percentage by weight of the sensory fragrance, with respect to the overall weight of the personal care composition, which is needed to create the desired response in a mammal, and in particular a human being having an age of about 1 week to about 12 years. Examples of desired responses include improved sleep, increased calmness, increased relaxation, and increased smiling. Preferably the effective amount is less than about 30%, by weight of the fragrance, more preferably between about 0.1% and about 10%, most preferably between about 0.2% and about 2%.

The "sensory fragrance" is comprised of volatile oils that may be extracted from a natural or synthetic source. The sensory fragrance may also further include other odoriferous components that may be used for purposes of improving the appeal to the consumer of the personal care compositions of the invention. The preferred sensory fragrance comprises, based upon the total weight of the sensory fragrance, from about 0.01% to about 30%, e.g., from about 0.1% to about 10%, and from about 0.1% to about 8% of the essential oils, and from about 70% to about 99.99%, e.g. from about 90% to about 99.9%, and from about 92% to about 99.9% of the other odoriferous components.

The preferred sensory fragrance is comprised of essential oils selected from one or more members of the group consisting of chamomile, rose, orange, tuberose, sandalwood, lavender, cedarwood, bergamot, and benzoin resin.

Typically, the essential oil portion of the sensory fragrance is comprised of, based upon the total weight of the total fragrance, from about 0.05% to about 5% chamomile, about 0.01% to about 5% rose, about 0.5% to about 30% orange, about 0.01% to about 5% tuberose, about 0.01% to about 25% sandalwood, about 0.01% to about 30% lavender, about 0.1% to about 30% cedarwood, about 0.01% to about 30% bergamot, and about 0.1% to about 15% benzoin resin. Alternatively, the essential oil portion of the sensory fragrance is comprised of, based upon the total weight of the total fragrance, from about 0.05% to about 3% chamomile, between about 0.01% to about 3% rose, between about 0.5% to about 15% orange, between about 0.01% to about 3% tuberose, between about 0.01% to about 15% sandalwood, between about 0.01% to about 15% lavender, between about 0.1% to about 30% cedarwood, between about 0.01% to about 15% bergamot, and between about 0.1% to about 10% benzoin resin. In another embodiment, the essential oil portion of the sensory fragrance is comprised of, based upon the total weight of the fragrance, from about 0.05% to about 2% chamomile, from about 0.01% to about 1.5% rose, from about 0.5% to about 10% orange, from about 0.01% to about 1.5% tuberose, from about 0.01% to about 10% sandalwood, from about 0.01% to about 10% lavender, from about 0.1% to about 30% cedarwood, from about 0.01% to about 10% bergamot, and from about 0.1% to about 5% benzoin resin.

The other odoriferous components of the sensory fragrance include but are not limited to benzenoid materials, alcohol materials, ester materials, aldehyde materials, ketone materials, and mixtures thereof. The benzenoid materials are selected from benzyl benzoate, benzyl carbinol, benzyl salicylate, benzyl cinnamate, diethyl phthalate, phenoxy ethanol, hexahydro-4,6,6,7,8,8-hexamethylcyclopenta-γ-2-benzopyran, 7-acetyl-1,1,3,4,4, 6-hexamethyltetralin, 3-(3,4-methylene dioxyphenol)-2-methyl propanol, methyl-iso-eugenol, eugenol, and mixtures thereof. The alcohol materials are selected from citronellol, alcohol C-8, alcohol C-10; alcohol C-11, alcohol C12, dipropylene glycol, linalool, geraniol, benzyl alcohol, 2-ethyl-4-(2,2,3-trimethyl-3-cyclopentene-1-yl)-2-buten-l-ol, dihydromyrcenol, and mixtures thereof. The aldehyde materials are selected from 4-(4-hydroxy-4-methylpentyl)-3-cyclohexene 1-carboxoaldehyde, p-t-butyl-α-methyidihydrocinnamic aldehyde, aldehyde C-10, aldehyde C-11, aldehyde C-12, laurinal, heliotropine, anisic aldehyde, benzyl aldehyde, and mixtures thereof. The esters materials are selected from benzyl acetate, dimethyl benzyl carbinyl acetate, ethylene brassylate, cyclopentadecanolide, linalyl acetate, benzyl proprionate, citronellyl acetate, hexyl butyrate, neryl acetate, prenyl acetate, hexyl cinnamate, oxacyclohexadecen-2-one, and mixtures thereof. The ketones materials are selected from methyl ionone, ambretone, methyl dihydro jasmonate, muscone, allyl ionone, and mixtures thereof.

The sensory fragrance may be produced by blending the selected essential oils and odoriferous components under ambient conditions until the final mixture is homogenous using equipment and methodology commonly known in the art of fragrance compounding. It is preferable to store the final sensory fragrance mixture under ambient conditions for a few hours after mixing before using it as a component of a personal care composition. The personal care compositions of the present invention may then be produced by blending the desired components with the sensory fragrance using equipment and methodology commonly known in the art of personal care product manufacture. In order to improve the solubilization of the sensory fragrance in aqueous personal care compositions, the sensory fragrance may be pre-blended with one or more of the nonionic surfactants.

"Personal care compositions" refers to personal cosmetic, toiletry, and healthcare products such as wipes, washes, baths, shampoos, gels, soaps, sticks, balms, sachets, pillows, mousses, sprays, lotions, creams, cleansing compositions, powders, oils, bath oils and other bath compositions which may be added to a bath. Personal care compositions may also include, but are not limited to, aerosols, candles, and substances that may be used with vaporizers. The aforementioned wipes, washes, baths, shampoos, gels, soaps, sticks, balms, sachets, pillows, mousses, sprays, lotions, creams, cleansing compositions, oils, bath oils, aerosols, candles and substances which may be used with vaporizers are commercially known to those who have a knowledge of preparing personal care compositions.

The preferred personal care compositions of the invention are lotions, powders, bath oils and other bath additives wherein the use of the personal care compositions of the present invention is capable of reducing the cortisol levels of a mammal by about 0.1% to about 75% after the personal care composition is administered to said mammal and/or those capable of increasing the sIgA levels of a mammal by about 10% to about 150%, preferably from about 20% to about 70%. The cortisol levels of a mammal are typically reduced within about 20 minutes to about 30 minutes after administration of the personal care composition of the present invention thereto. The sIgA levels of a mammal are typically increased within about 1 minute to about 10 minutes after administration of the personal care composition of the present invention thereto. The sIgA levels may be measured in accordance with sIgA methods known in the art such as, for example, those disclosed in Stone, which is incorporated by reference herein.

In order to achieve the desired response in a mammal, the personal care composition may be used in a dosing amount that is in accordance with the prescribed directions of the personal care composition.

Particularly, the invention includes a method of increasing smiling of a human having an age of about 1 day to about 12 years comprising administering to said human a personal care composition which comprises an effective amount of the sensory fragrance. The preferred age of a human whose smiling is increased by this invention is about 1 week to about 5 years, more preferably about 1 week to about 3 years, most preferably between about 1 week to about 2 years.

Further, the invention includes a method of reducing crying in a human having an age of about 1 day to about 12 years comprising administering to said human a personal care composition which comprises an effective amount of the sensory fragrance. The preferred age of a human whose crying is reduced by this invention is about 1 week to about 5 years, more preferably about 1 week to about 3 years, most preferably between about 1 week to about 2 years.

Still further, the invention includes a method of improving sleep behaviors in a mammal including a human and in particular a human having an age of about 1 day to about 12 years comprising administering to said mammal a personal care composition which comprises an effective amount of the sensory fragrance. The preferred age of a human whose sleep behaviors are improved by this invention is about 1 week to about 5 years, more preferably about 1 week to about 3 years, most preferably between about 1 week to about 2 years.

Yet still further, the invention includes a method of soothing a mammal, and in particular a human having an age of about 1 day to about 12 years, comprising administering to said mammal a personal care composition which comprises an effective amount of the sensory fragrance. The preferred age of a human who is soothed by this invention is about 1 week to about 5 years, more preferably about 1 week to about 3 years, most preferably between about 1 week to about 2 years. The term "soothing" as used herein, refers to bringing peace, composure, relief, or quietude to a human having an age of about 1 day to about 12 years. It is generally apparent that when children in particular are soothed, they cry less, and sleep better.

In addition, the invention includes a personal care composition comprising an effective amount of the sensory fragrance, where the sensory fragrance comprises essential oils selected from one or more members of the group consisting of chamomile, rose, orange, tuberose, sandalwood, lavender, cedarwood, bergamot, and benzoin resin. The preferred sensory fragrance of the invention contains the essential oils chamomile, rose, orange, tuberose, sandalwood, lavender, cedarwood, bergamot, and benzoin resin.

Still further, the invention includes a personal care composition comprising an effective amount of the sensory fragrance, where the sensory fragrance comprises essential oils selected from one or more members of the group consisting of chamomile, rose, orange, tuberose, sandalwood, lavender, cedarwood, bergamot, and benzoin resin, where said personal care composition reduces the cortisol levels of a mammal by about 0.1% to about 75%, e.g. from about 20% to about 40%, from about 10% to about 50%, or from about 15% to about 35% and/or increases the level of sIgA by about 10% to about 150%, e.g. from about 20% to about 70% or from about 40% to about 55%. Preferably, the reduction of cortisol level and the increase in IgA level are measured in the saliva of a mammal.

Another additional aspect of the invention includes a method of increasing the smiling of a human comprising administering to said human a personal care composition comprising an effective amount of the sensory fragrance wherein the sensory fragrance comprises essential oils selected from one or more members of the group consisting of chamomile, rose, orange, tuberose, sandalwood, lavender, cedarwood, bergamot, benzoin resin.

Still further, the invention includes a method of calming a mammal comprising administering to said human a personal care composition comprising an effective amount of the sensory fragrance wherein the sensory fragrance comprises essential oils selected from one or more members of the group consisting of chamomile, rose, orange, tuberose, sandalwood, lavender, cedarwood, bergamot, and benzoin resin, where said personal care composition reduces the cortisol levels of a mammal by about 0.1% to about 75% and/or increases the sIgA levels of a mammal by about 10% to about 150%.

One method of soothing a mammal, in particular a human having an age of 1 week to about 1 year, is via the use of the personal care composition of the present invention that is comprised of, based upon the total weight of the personal care composition, from about 98.5% mineral oil and about 1.5% of the sensory fragrance, which is preferably comprised of the following essential oils in amounts based upon the total weight of the fragrance: about 1% chamomile, about 0.75% rose, about 5% orange, about 0.5% tuberose, about 7.5% sandalwood, about 8% lavender, about 4.8% cedarwood, about 9.6% bergamot, and about 0.7.% benzoin resin. The personal care composition may be massaged or rubbed onto the skin of a human being at any time, but typically the personal care composition is administered before bedtime.

In order to illustrate the invention the following examples are included. These examples do not limit the invention. They are meant only to suggest a method of practicing the invention. Those knowledgeable in the calming of human beings as well as other specialties may find other methods of practicing the invention. Those methods are deemed to be within the scope of this invention.

EXAMPLES

Example 1

Preparation of Personal Care Composition A with Sensory Fragrance

Takasago Fragrance #RK-2086/1, (containing 50% benzenoid material, 25% alcohol material, 12% ester material, 7% aldehyde material, 5% essential oils, and 1% ketone material) was mixed with a cleansing surfactant composition. This cleaning surfactant composition contains sodium lauroamphodiacetate, sodium laureth-13 carboxylate, sodium trideceth sulfate, polysorbate-20, PEG-150 distearate, POE 80 sorbitan monolaurate, cocamidopropyl betaine, tetrasodium EDTA, quaternium 15, citric acid, USP, sodium chloride, and water where the percentages of components in the personal care composition are listed in Table A.

TABLE A

| INCI Name | % Active | % (wt/wt) | % Active (wt/wt) |
| --- | --- | --- | --- |
| Disodium Lauroamphodiacetate | 30 | 2.700 | 0.810 |
| Sodium Laureth-13 Carboxylate | 70 | 1.350 | 0.945 |
| Sodium Trideceth Sulfate | 30 | 9.000 | 2.700 |
| Polysorbate-20 | 100 | 0.500 | 0.500 |
| PEG-150 Distearate | 100 | 0.700 | 0.700 |
| POE 80 Sorbitan Monolaurate | 72 | 6.000 | 4.320 |
| Fragrance | 100 | 1.000 | 1.000 |
| Cocamidopropyl Betaine | 30 | 12.50 | 3.750 |
| Tetrasodium EDTA | 38 | 0.200 | 0.076 |
| Quaternium 15 | 100 | 0.049 | 0.049 |
| Citric Acid, USP | 100 | 0.200 | 0.20 |
| Sodium Chloride | 100 | 2.000 | 2.00 |
| Water | 0 | 63.80 | 0 |

Example 2

Preparation of Personal Care Composition B without Sensory Fragrance

Personal Care Composition B contains a cleaning surfactant system which contains: Disodium Lauroamphodiacetate, Sodium Laureth-13 Carboxylate, Sodium Trideceth Sulfate, Polysorbate-20, PEG-150 Distearate, POE 80 Sorbitan Monolaurate, Fragrance, Cocamidopropyl Betaine, Tetrasodium EDTA, Quaternium 15, Citric Acid, USP, Sodium Chloride, and Water in the same relative ratios as the 99% portion of Personal Care Composition A.

Example 3

Bathing Infants with Personal Compositions A and B and Determining Their Salivary Cortisol Levels Saliva samples were taken from groups of children having an age of 1 week to 4 months and their care givers. Said saliva was tested to determine the baseline salivary cortisol levels. Subsequently, the same infants were given a bath by their caregivers using Personal Care Composition B. Saliva samples were collected 20 minutes after the bathing procedure and salivary cortisol levels were measured. This group is the control group, Group 2.

Saliva samples were taken from another group of children of a similar age. Subsequently, these children were bathed with Personal Care Composition A. Saliva samples were collected 20 minutes after the bathing procedure and salivary cortisol levels were measured. This group is the testing group, Group 1.

The changes in cortisol levels of the infants and caregivers in Group 1 and Group 2 are shown in Table I.

TABLE I

Salivary Cortisol Level Change (Post bath - Initial)

| Subject | Group I (% CCL***) | Group 2 (% CCL) |
|---|---|---|
| Mother* | $-8.2 \pm 7.0^2$ | $-0.4 \pm 4.3$ |
| Child** | $-15.4 \pm 19.7^1$ | $+19.6 \pm 29.3$ |

[1]Group 1 demonstrates a statistically significant change from initial at a 94% confidence interval.
[2]Group 1 demonstrates a statistically significant change from initial at a 99% confidence interval.
*Group 1 demonstrates statistically significant difference from Group 2 at 99% confidence interval
**Group 1 demonstrates statistically significant difference from Group 2 at 98% confidence interval
***"CCL" means the change in cortisol level.

Example 4

Observed Behaviors of Infants and Caregivers

Another group of 10 children and their caregivers followed the bathing procedures of Example 3. The bathing procedures were monitored on videotape. Children and their caregivers were observed and the results were tabulated in Table II.

TABLE II

Observed behavior during bath

| Behavior | Group 1 (% Occurrence) | Group 2 (% Occurrence) |
|---|---|---|
| Mother Smiling | $37.0 \pm 25.1$ | $16.4 \pm 13.9$ |
| Mother Touching Baby[2] | $90.2 \pm 11.5$ | $65.2 \pm 20.7$ |
| Child Looking at Mother[1] | $87.4 \pm 5.9$ | $65.0 \pm 26.8$ |

[1]Group 1 demonstrates statistically significant difference from Group 2 at 90% confidence interval.
[2]Group 1 demonstrates statistically significant difference from Group 2 at 95% confidence interval.
[3]Group 1 demonstrates statistically significant difference from Group 2 at 99% confidence interval.

Example 5

Sleep Behaviors after Bathing

Another group of 10 children and their caregivers followed the bathing procedure of example 3. After the bath the children were placed in a quiet place and were allowed to go to sleep. During this period, sleep measurements, including sleep delay behaviors, the latency of sleep (time until onset), sleep stages (grimacing and movements) and activity level were observed and are tabulated below.

TABLE II

Observed behavior after bath

| Behavior | Group 1 (% Occurrence) | Group 2 (% Occurrence) |
|---|---|---|
| Infant in Deep Sleep[3]* | $42.2 \pm 15.8$ | $9.4 \pm 17.3$ |
| Infant Crying | $28.4 \pm 30.8$ | $52.1 \pm 38.7$ |

[1]Group 1 demonstrates statistically significant difference from Group 2 at 90% confidence interval.
[2]Group 1 demonstrates statistically significant difference from Group 2 at 95% confidence interval.
[3]Group 1 demonstrates statistically significant difference from Group 2 at 99% confidence interval.
*By "deep sleep" it is meant that the subject infant rested in a relaxed manner with minimal grimacing and movements.

Upon review of the records for the studies performed in accordance with Examples 1 through 5, it was unclear whether or not these studies were performed in accordance with the prescribed protocol. In view of this uncertainty, similar additional studies were performed as set forth below in Examples 6–8.

Example 6

Fragranced Bath and Saliva Collection

A total of eleven male and female children having an age of about 9 to 11 years participated in a bathing study in which their respective saliva samples were collected both before and after bathing for the purpose of measuring salivary cortisol concentrations and salivary sIgA concentrations.

Immediately prior to bathing, about 1 ml of an initial saliva sample was collected from each respective child via having each child drool or spit into an independent vial. These samples were then frozen until subsequent cortisol concentration and sIgA analyses.

Each child was then asked to bathe independently for a period of 10 minutes in a bath of water having a temperature of 33° C. to 35° C. The bath had been filled to a level approximately mid way on each child's torso when seated in the bathtub. Sixty grams of the fragranced bath of Example 1 were then added to the bath.

Thirty minutes after each child had finished bathing, about 1 ml of a post-bathing saliva sample was collected from each child via having each child drool or spit into a second independent vial. This second sample was also frozen for subsequent cortisol and IgA concentration analyses.

Example 7

Bathing with Unfragranced Bath and Collection

A total of 10 male and female children having an age of about 9 to 11 years participated in a second bathing study in which their saliva samples were collected both before and after bathing for the purpose of measuring salivary cortisol concentrations and salivary sIgA concentrations. Each child repeated the procedure set forth in Example 6, with the exception that an unfragranced bath of Example 2 was added to the bath in place of the fragranced bath.

Example 8

Salivary Cortisol Testing

Saliva samples obtained from the studies of Example 6 and Example 7 were tested for cortisol concentrations by Salimetrics, LLC using a "SALIMETRICS HS-CORTISOL HIGH SENSITIVITY SALIVARY CORTISOL ENZYME IMMUNOASSAY KIT" available from Salimetrics, LLC in its catalog as "Catalog No. 0101 96-Well Kit" in accordance with the instructions contained therein.

The results of the cortisol analyses for examples 7 and 8 are reported in Tables III and IV.

TABLE III

| Example 6 | Cortisol ($\mu$g/dl) | | |
|---|---|---|---|
| Panelist # | Before | After | Change |
| A | 0.472 | 0.243 | −0.229 |
| B | 0.084 | 0.113 | 0.029 |
| C | 0.538 | 0.187 | −0.351 |
| D | 0.149 | 0.112 | −0.037 |
| E | 0.16 | 0.128 | −0.032 |
| F | 0.134 | 0.13 | −0.004 |
| G | 0.29 | 0.176 | −0.114 |
| H | 0.174 | 0.131 | −0.043 |
| I | 0.145 | 0.076 | −0.069 |
| J | 0.274 | 0.214 | −0.06 |
| K | 0.208 | 0.158 | −0.05 |

TABLE IV

| Example 8 | Cortisol ($\mu$g/dl) | | |
|---|---|---|---|
| Panelist # | Before | After | Change |
| A | 0.703 | 0.251 | −0.452 |
| B | 0.191 | 0.116 | −0.075 |
| C | 0.128 | 0.12 | −0.008 |
| D | 0.177 | 0.073 | −0.104 |
| E | 0.207 | 0.098 | −0.109 |
| F | 0.074 | 0.049 | −0.025 |
| G | 0.202 | 0.097 | −0.105 |
| H | 0.156 | 0.081 | −0.075 |
| I | 0.125 | 0.091 | −0.034 |
| J | 0.195 | 0.119 | −0.076 |
| K | 0.147 | 0.087 | −0.06 |

This Example showed that both bath products were effective at reducing the cortisol levels of the children.

Example 9

Salivary sIgA Analysis

Saliva samples obtained from the studies of Example 6 and Example 7 were tested for salivary sIgA concentrations by Salimetrics, LLC in accordance with the protocol below and the materials and protocol provided in the kit of Example 8.

After thawing the saliva samples from a temperature of −80° C., the samples were vortexed, and centrifuged at 1500×g for 15 minutes. A 1:2000 dilution of the saliva was made using the buffer solution. 100 $\mu$l of calibrators and diluted saliva samples were then added to a microtiter plate coated with polyclonal rabbit antibodies to sIgA and incubated for 1 hour, with constant shaking at room temperature. After incubation, the plate was aspirated and washed 5× with 250 $\mu$l wash buffer to remove all unbound substances. 100 $\mu$l of peroxidase-labelled anti-sIgA antibody was then added to each well on the microtiter plate. After incubating the plate for 30 minutes with constant shaking at room temperature, the contents of the plate were decanted and washed 5× with the 250 $\mu$l wash buffer to remove all unbound substances. 100 $\mu$l of tetramethylbenzidine (TMB) substrate solution was added and incubated for 15–20 minutes at room temperature with no mixing. This enzyme acted on the substrate and caused a blue color to appear in proportion to the amount of peroxidase present. 50 $\mu$l of the stop solution was then added to the wells and the OD (optical density) was read on the plate reader at 450 nm. A yellow color was formed after stop solution was added. The amount of color detected was directly proportional to the amount of sIgA present.

Using values obtained from the calibrators, a dose response curve of the optical density verses concentration was then plotted. The level of secretory IgA in each sample was then determined from this curve.

The results of the sIgA analyses for examples 6 and 7 were are reported in Tables V and VI below.

TABLE V

| Example 6 | sIgA ($\mu$g/ml) | | |
|---|---|---|---|
| Panelist # | Before | After | Change |
| A | 275.67 | 145.93 | −129.74 |
| B | None detected | 223.31 | Not applicable |
| C | 499.59 | 261.58 | −238.01 |
| D | 518.77 | 451.78 | −66.99 |
| E | 408.05 | 124.21 | −283.84 |
| F | 954.27 | 522.98 | −431.29 |
| G | 221.64 | 99.33 | −122.31 |
| H | 119.05 | 119.08 | 0.03 |
| I | 106.66 | 219.09 | 112.43 |
| J | 201.74 | 279.83 | 78.09 |
| K | 167.8 | 206.62 | 38.82 |

TABLE VI

| Example 7 | sIgA ($\mu$g/ml) | | |
|---|---|---|---|
| Panelist # | Before | After | Change |
| A | None detected | 139.32 | Not applicable |
| B | 386.33 | 748.7 | 362.37 |
| C | 92.62 | 120.04 | 27.42 |
| D | 746.25 | 267.14 | −479.11 |
| E | 310.79 | 461.91 | 151.12 |
| F | 254.18 | 171.65 | −82.53 |
| G | 407.92 | 369.79 | −38.13 |
| H | 221.04 | 211.2 | −9.84 |
| I | 687.59 | 194.51 | −493.08 |
| J | 627.52 | None detected | Not applicable |
| K | 260.37 | 196.3 | −64.07 |

This Example did not reveal a consistent trend in the change of sIgA concentration. While not wishing to be bound to the theory, it was considered that the 30 minute time point for saliva collection for sIgA might have been too long from the period of exposure. Therefore, it was decided to repeat the sIgA analyses, but with a shorter time period between exposure and sIgA sampling. The results of these studies are set forth in Examples 10 to 13 below.

Example 10

Effect of Sensory Fragrance on sIgA

Approximately 1 ml of saliva was collected in vials from a total of 8 male and female adults by having each adult drool or spit into an independent vial. The samples were frozen until later analyzed for sIgA concentration.

Each adult was then asked to frequently smell an open container containing the sensory fragrance used in the composition of Example 1 over a 5 minute period. Ten minutes after the completion of smelling the container, a second saliva sample was collected from each adult in an independent vial and stored as set forth above.

Five minutes following collection of the second saliva sample, a third saliva sample was collected from each adult and stored as set forth above.

Example 11

Effect of Unfragranced Composition on sIgA

The procedure of Example 10 was repeated with a total of 8 additional male and female adults, but the sensory fragrance was replaced with the unfragranced bath composition of Example 2.

Example 12

Effect of a Bath on sIgA

Approximately 1 ml of saliva was collected in vials from a total of eight male and female adults by having each adult drool or spit into an independent vial. The samples were frozen as set forth above in Example 6 until later analyzed for sIgA concentration.

Each volunteer was then asked to bathe in a tub of warm water for a period of 15 minutes.

Ten minutes after having finished bathing, a second saliva sample was collected and stored set forth above.

Example 13

Effect of a Bath with Fragranced Bath on sIgA

Approximately 1 ml of saliva was collected in vials from a total of eight male and female adult volunteers by having each adult drool or spit into an independent vial. The samples were then frozen set forth above in Example 6 until later analyzed for sIgA concentration.

Each volunteer was then asked to bathe in a tub of warm water containing 30 g of the bath composition of Example 1 for a period of 15 minutes.

Ten minutes after having finished bathing, a second saliva sample was collected and stored in the same way as the first saliva sample.

The samples were then analyzed for sIgA as described above in Example 9. The results of the sIgA analyses for examples 10, 11, 12, and 13, respectively, are reported in Tables VII, VIII, IX, and X, respectively, below.

TABLE VII

Sensory Fragrance

Example 10 SlgA ($\mu$g/ml)

| Panelist # | Before | After | Change |
|---|---|---|---|
| 1 | 214.35 | 155.25 | −59.1 |
| 2 | 79.11 | 178.32 | 99.21 |
| 3 | 81.05 | 168.06 | 87.01 |
| 4 | 129.64 | 271.23 | 141.59 |
| 5 | 167.75 | 167.01 | −0.74 |
| 6 | 194.94 | 178.18 | −16.76 |
| 7 | 85.03 | 175.74 | 90.71 |
| 8 | 174.97 | 110.18 | −64.79 |

TABLE VIII

No sensory fragrance

Example 11 SlgA ($\mu$g/ml)

| Panelist # | Before | After | Change |
|---|---|---|---|
| 1 | 159.9 | 153.82 | −6.08 |
| 2 | 261.33 | 200.93 | −60.4 |
| 3 | 150.58 | 131.4 | −19.18 |
| 4 | 469.66 | 208.61 | −261.05 |
| 5 | 212.73 | 350.69 | 137.96 |
| 6 | 107.1 | 108.94 | 1.84 |
| 7 | 172.57 | 147.3 | −25.27 |
| 8 | 66.29 | 107.93 | 41.64 |

The data in Tables VII and VIII demonstrate that the sIgA concentrations of the panelists significantly increased by an average of about 47% after each adult inhaled the sensory fragrances of the present invention. The average increase in sIgA for panelists who inhaled the unfragranced material was only about 2%. This data was found to be statistically significant at a confidence level of 85%. This Example showed that the present invention is effective in increasing sIgA concentrations, which also correlates with a reduction of stress.

TABLE IX

Bath

Example 12 slgA ($\mu$g/ml)

| Panelist # | Before | After | Change |
|---|---|---|---|
| 1 | 201.97 | 113.15 | −88.82 |
| 2 | 237.69 | 218.85 | −18.84 |
| 3 | 163.75 | 205.96 | 42.21 |
| 4 | 488.34 | 115.3 | −373.04 |
| 5 | 165.52 | 94.93 | −70.59 |
| 6 | 45.44 | 52.63 | 7.19 |
| 7 | 116.67 | 86.2 | −30.47 |
| 8 | 113.43 | 166.48 | 53.05 |

TABLE X

Fragranced Bath

Example 13 slgA ($\mu$g/ml)

| Panelist # | Before | After | Change |
|---|---|---|---|
| 1 | 89.48 | 79.42 | −10.06 |
| 2 | 142.61 | 164.79 | 22.18 |
| 3 | NA | NA | NA |
| 4 | 415.78 | 191.19 | −224.59 |
| 5 | 219.77 | 254.56 | 34.79 |
| 6 | 60.8 | 108.38 | 47.58 |
| 7 | 70.45 | 56.2 | −14.25 |
| 8 | 126.78 | 158.21 | 31.43 |

The data in Tables IX and X showed that the sIgA changes for the panelists who bathed in water containing the sensory fragrances of the present invention were comparable to those recorded by the panelists who bathed in the water alone.

Each of the panelists who participated in the studies of Examples 10 to 13 were also given a questionnaire regarding how they each felt after the completion of the study. More specifically, the questionnaire addressed whether or not the panelists felt good, soothed, relaxed, more at ease, less stressed, safe, comforted, and/or calm after inhaling the compositions (either alone or in a bath) of the study. The results of the questionnaire for panelists who only inhaled compositions (e.g. those of Examples 10 and 11) are shown in Table XI. The results of the questionnaire for panelists who inhaled compositions while bathing therein (e.g. those of Examples 12 and 13) are shown in Table XII.

TABLE XI

| Sniff Test | Percent of Panelists who agreed | |
| --- | --- | --- |
| Feeling | Unfragranced | Fragranced |
| Soothed | 38 | 75 |
| Relaxed | 50 | 88 |
| More At Ease | 38 | 88 |
| Feel Good | 75 | 75 |
| Less Stressed | 38 | 75 |
| Safe | 25 | 25 |
| Comforted | 25 | 63 |
| Calm | 38 | 88 |

TABLE XII

| Bath Test | Percent of Panelists who agreed | |
| --- | --- | --- |
| Feeling | Unfragranced | Fragranced |
| Soothed | 57 | 88 |
| Relaxed | 86 | 100 |
| More At Ease | 100 | 75 |
| Feel Good | 86 | 100 |
| Less Stressed | 57 | 100 |
| Safe | 29 | 38 |
| Comforted | 43 | 75 |
| Calm | 71 | 75 |

This example showed that the panelists who inhaled the sensory fragrances (either with or without a bath) felt better and had a more positive experience than those panelists who did not inhale the sensory fragrance. Most significantly, as shown in Table XII, all of the panelists reported to have felt relaxed, good, and less stressed after inhaling the sensory composition in a bath.

What is claimed is:

1. A method of relaxing a mammal comprising administering to said mammal a personal care composition which comprises an effective amount of a sensory fragrance, wherein the sensory fragrance is comprised of, based upon the total weight of the sensory fragrance, from about 0.1% to about 8% of an essential oil portion and from about 92% to about 99.9% of an odoriferous portion, wherein the essential oil portion is comprised of, based upon the total weight of the sensory fragrance, from about 0.05% to about 5% chamomile and about 0.01% to about 30% lavender, and wherein the personal care composition is capable of reducing the cortisol level of the mammal by about 0.1% to about 75% and/or increasing the sIgA level of the mammal by about 10% to about 150%.

2. The method of claim 1 wherein the essential oil portion is comprised of, based upon the total weight of the sensory fragrance, from about 0.05% to about 2% chamomile and about 0.01% to about 10% lavender.

3. A method of relaxing a mammal comprising administering to said mammal a personal care composition which comprises an effective amount of a sensory fragrance, wherein the sensory fragrance is comprised of, based upon the total weight of the sensory fragrance, from about 0.1% to about 8% of an essential oil portion and from about 92% to about 99.9% of an odoriferous portion, wherein the essential oil portion is comprised of, based upon the total weight of the sensory fragrance, from about 0.01% to about 1.5% rose, and wherein the personal care composition is capable of reducing the cortisol level of the mammal by about 0.1% to about 75% and/or increasing the sIgA level of the mammal by about 10% to about 150%.

4. A method of relaxing a mammal comprising administering to said mammal a personal care composition which comprises an effective amount of a sensory fragrance, wherein the personal care composition is capable of reducing the cortisol level of the mammal by about 0.1% to about 75% and/or increasing the sIgA level of the mammal by about 10% to about 150%, wherein the personal care composition is a shampoo.

5. A method of relaxing a mammal comprising administering to said mammal a personal care composition which comprises an effective amount of a sensory fragrance, wherein the personal care composition is capable of reducing the cortisol level of the mammal by about 0.1% to about 75% and/or increasing the sIgA level of the mammal by about 10% to about 150%, wherein the personal care composition is a powder.

6. A method of relaxing a mammal comprising administering to said mammal a personal care composition which comprises an effective amount of a sensory fragrance, the sensory fragrance being comprised of, based upon the total weight of the sensory fragrance, from about 0.1% to about 8% of an essential oil portion and from about 92% to about 99.9% of an odoriferous portion, the odoriferous portion containing one or more benzenoid materials, alcohol materials, ester materials, aldehyde materials, ketone materials, or mixtures thereof, wherein the personal care composition is capable of reducing the cortisol level of the mammal by about 0.1to about 75% and/or increasing the sIgA level of the mammal by about 10% to about 150% wherein the personal care composition is a shampoo.

7. A method of relaxing a mammal comprising administering to said mammal a personal care composition which comprises an effective amount of a sensory fragrance, the sensory fragrance being comprised of, based upon the total weight of the sensory fragrance, from about 0.1% to about 8% of an essential oil portion and from about 92% to about 99.9% of an odoriferous portion, the odoriferous portion containing one or more benzenoid materials, alcohol materials, ester materials, aldehyde materials, ketone materials, or mixtures thereof, wherein the personal care composition is capable of reducing the cortisol level of the mammal by about 0.1to about 75% and/or increasing the sIgA level of the mammal by about 10% to about 150%, wherein the personal care composition is a wash or bath.

8. A method of relaxing a mammal comprising administering to said mammal a personal care composition which comprises an effective amount of a sensory fragrance, the sensory fragrance being comprised of, based upon the total weight of the sensory fragrance, from about 0.1% to about 8% of an essential oil portion and from about 92% to about 99.9% of an odoriferous portion, the odoriferous portion containing one or more benzenoid materials, alcohol materials, ester materials, aldehyde materials, ketone materials, or mixtures thereof, wherein the personal care composition is capable of reducing the cortisol level of the mammal by about 0.1to about 75% and/or increasing the sIgA level of the mammal by about 10% to about 150%, wherein the personal care composition is a powder.

9. A method of relaxing a mammal comprising administering to said mammal a personal care composition which comprises an effective amount of a sensory fragrance, the sensory fragrance being comprised of, based upon the total weight of the sensory fragrance, from about 0.1% to about 8% of an essential oil portion and from about 92% to about 99.9% of an odoriferous portion, the odoriferous portion containing one or more benzenoid materials, alcohol materials, ester materials, aldehyde materials, ketone materials, or mixtures thereof, wherein the personal care composition is capable of reducing the cortisol level of the mammal by about 0.1 to about 75% and/or increasing the sIgA level of the mammal by about 10% to about 150%, wherein the personal care composition is a lotion.

10. A method of relaxing a mammal comprising administering to said mammal a personal care composition which comprises an effective amount of a sensory fragrance, the sensory fragrance being comprised of, based upon the total weight of the sensory fragrance, from about 0.1% to about 8% of an essential oil portion and from about 92% to about 99.9% of an odoriferous portion, the odoriferous portion containing one or more benzenoid materials, alcohol materials, ester materials, aldehyde materials, ketone materials, or mixtures thereof, wherein the personal care composition is capable of reducing the cortisol level of the mammal by about 0.1 to about 75% and/or increasing the sIgA level of the mammal by about 10% to about 150%, wherein the personal care composition is a wipe.

* * * * *

UNITED STATES PATENT AND TRADEMARK OFFICE
Certificate

Patent No. 6,830,755 B2                                    Patented: December 14, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Joseph Librizzi, Neshanic, NJ; Benjamin Carl Wiegand, Newtown, PA; Teresita Diaz, Perth Amboy, NJ; Laura McCulloch, Kings Somborne, United Kingdom; John Hopkins, Newbury, United Kingdom; Theodore L. Barba, Old Brookville, NY; Anthony Joseph Leardi, Middletown, NY; William Appert, Kinnelon, NJ; Tetsuo Nakatsu, Chappaqua, NY; and Debi Parr, Lexington, MA.

Signed and Sealed this Seventh Day of March 2006.

GARY L. KUNZ
*Supervisory Patent Examiner*
Art Unit 1616

UNITED STATES PATENT AND TRADEMARK OFFICE
CERTIFICATE OF CORRECTION

PATENT NO. : 6,830,755 B2
DATED : December 14, 2004
INVENTOR(S) : Librizzi et al.

It is certified that error appears in the above-identified patent and that said Letters Patent is hereby corrected as shown below:

Title page,
Item [76], Inventors, should read
-- Joseph Librizzi, Neshanic, NJ; Benjamin Carl Wiegand, Newtown, PA; Teresita Diaz, Perth Amboy, NJ; Laura McCulloch, Kings Somborne, United Kingdom; John Hopkins, Newbury, United Kingdom; Theodore L. Barba, Old Brookville, NY; Anthony Joseph Leardi, Middletown NY; William Appert, Kinnelon, Kinnelon, NJ; Tetsuo Nakatsu, Chappaqua, NY; and Debi Parr, Lexington, MA --.

Signed and Sealed this

Thirtieth Day of May, 2006

JON W. DUDAS
*Director of the United States Patent and Trademark Office*